United States Patent [19]

Gould

[11] Patent Number: 4,790,196

[45] Date of Patent: Dec. 13, 1988

[54] SAMPLER OF PARTICULATE MATERIAL ON A MOVING BELT

[76] Inventor: Gregory Gould, 30 Clairmont Ave., Thornwood, N.Y. 10594

[21] Appl. No.: 92,663

[22] Filed: Sep. 3, 1987

[51] Int. Cl.[4] .............................................. G01N 1/12
[52] U.S. Cl. .............................. 73/863.91; 73/863.53; 73/864.32
[58] Field of Search ........... 73/863.53, 863.91, 863.92, 73/864.32; 198/713, 497, 499

[56] References Cited

U.S. PATENT DOCUMENTS

| | | | |
|---|---|---|---|
| 2,889,709 | 6/1959 | Blyth | 73/863.91 |
| 3,181,369 | 5/1965 | Taylor | 73/863.91 |
| 3,280,635 | 10/1966 | Cochet | 73/863.91 |
| 3,545,280 | 12/1970 | Gosney | 73/863.91 |

Primary Examiner—Stewart J. Levy
Assistant Examiner—Robert P. Bell
Attorney, Agent, or Firm—John L. Gray

[57] ABSTRACT

A device for periodically obtaining samples of particulate material from a moving belt comprising a sample cutter provided with an opening at one end, and means for moving said sample cutter across the moving belt and minimizing the effects resulting from disturbance of said material on the belt and maximizing the effective opening of the sample cutter by minimizing the amount of particulate material accumulating in front of the sample cutter as it moves across the moving belt, and means for minimizing the accumulation of particulate material on the side of the sample cutter positioned upstream of the movement of the particulate material on said moving belt.

3 Claims, 2 Drawing Sheets

U.S. Patent     Dec. 13, 1988     Sheet 1 of 2     4,790,196
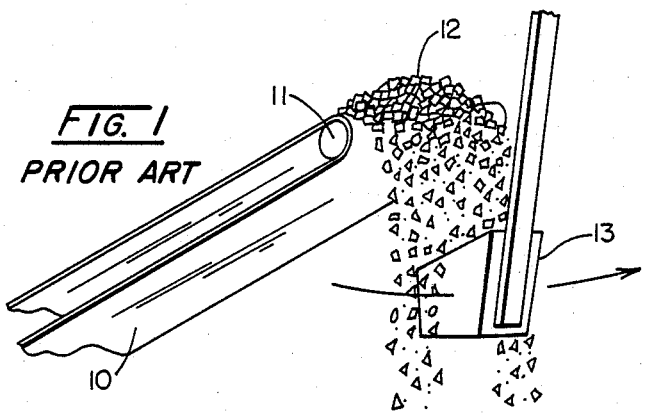
FIG. 1
PRIOR ART
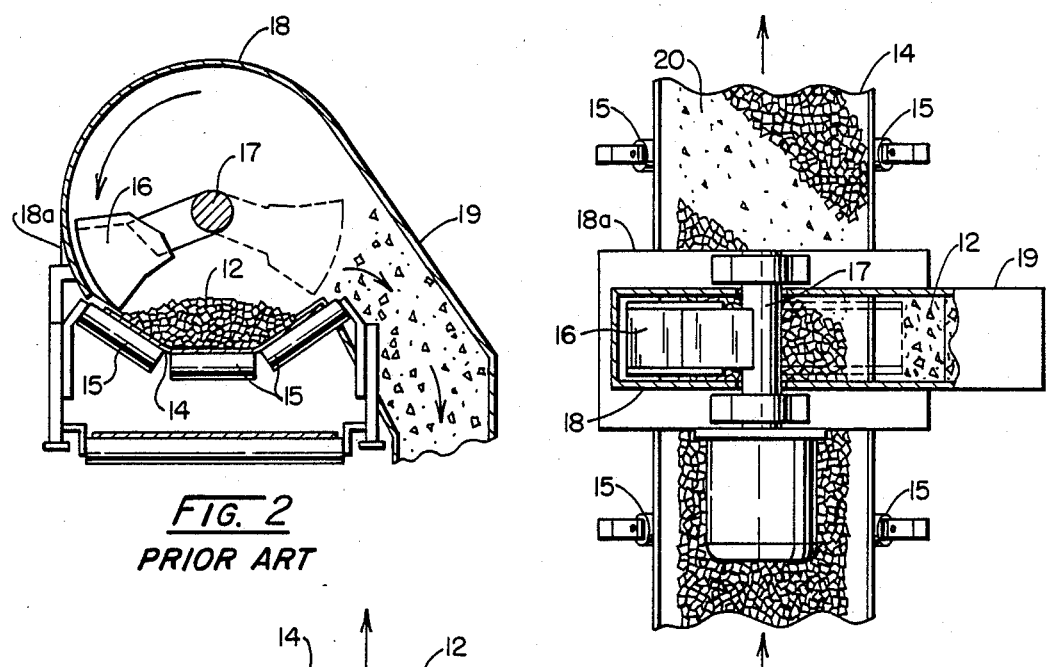
FIG. 2
PRIOR ART
FIG. 3
PRIOR ART
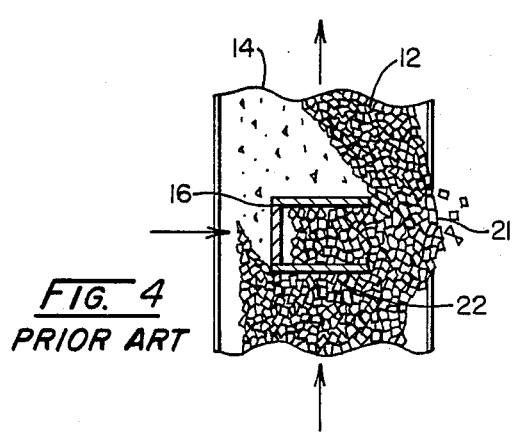
FIG. 4
PRIOR ART

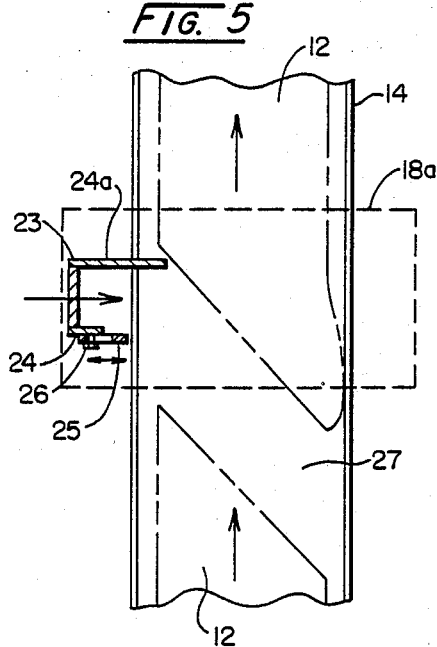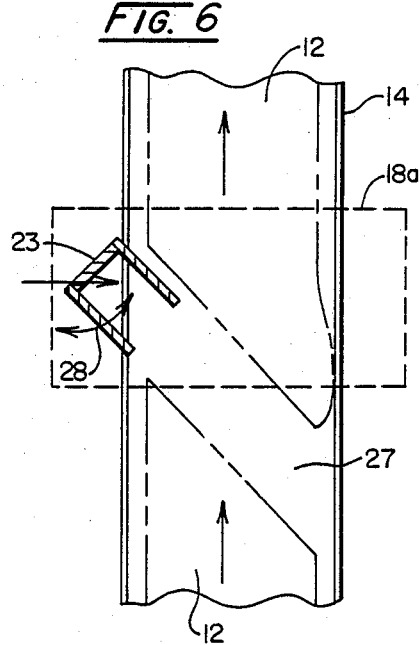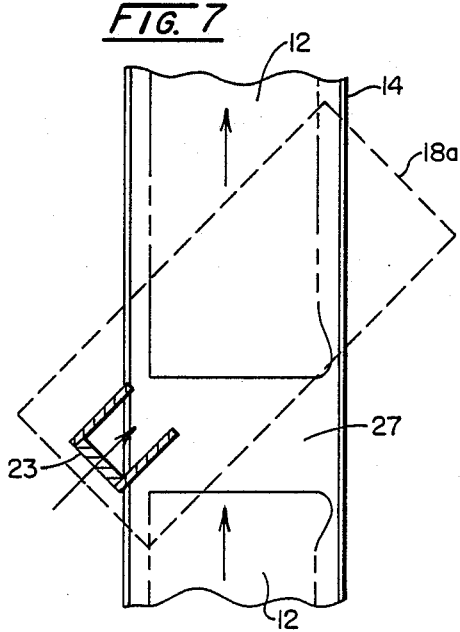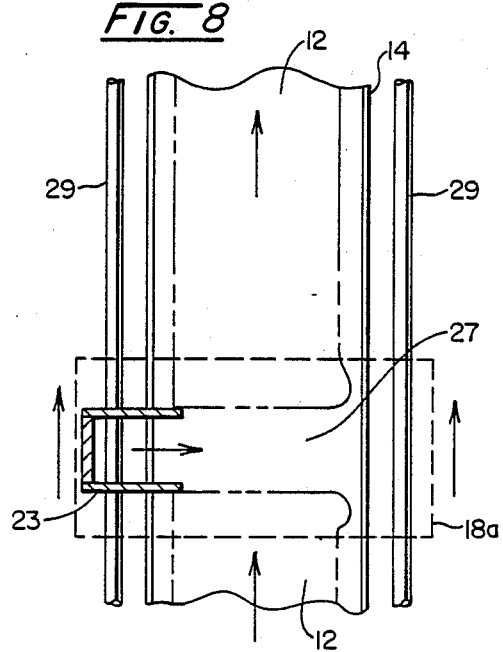

SAMPLER OF PARTICULATE MATERIAL ON A MOVING BELT

BACKGROUND OF THE INVENTION

It is customary to obtain samples of particulate material periodically from a moving belt to determine whether or not the particulate material meets specifications agreed upon by the supplier. Particulate materials may take a variety of forms such as ore, wheat, grain, coal, slurries, fertilizer, etc. While the invention set forth in this application has specific application to the sampling of coal in electric utilities, it is to be understood that the invention is not to be so limited, but has application to particulate material in any size range and when mixed with a liquid.

In the past, samples have been obtained by the free fall method wherein the particulate materials are carried on a moving belt to a point where the particulate material drops off the belt down to another moving belt and a bucket-shaped sample collector or moving diversion chute traverses the falling stream and collects the samples.

The major disadvantages of this system are the amount of headroom (from 7 to 20 feet) that is required and the cost of supporting structures and extra conveyors that are necessary.

As a consequence, in recent years the hammer or swing sampler has been gaining a certain amount of popularity. This sampler may be attached to any existing moving conveyor belt and rotates at right angles to the belt and periodically sweeps off a sample of particulate material into a chute for sampling.

The disadvantages of this device are that the effective opening of the sample cutter is limited because while it is also moving at right angles to the belt, the belt, of course, is also moving and, as a consequence, a diagonal path is cut through the particulate material on the belt resulting in a snowplowing action in front of the sample collector and a damming action on the upstream side of the sample collector as it moves across the belt. The use of the term "upstream" herein means the location from which the particulate material is moving on the belt. The term "downstream" means the location to which the particulate material is being taken. Thus the effective opening of this type of sample collector is significantly reduced and the constituents being sampled that are acquired by the sample cutter tend not to be in exactly the same proportions that they exist in the material being sampled. When a sample cutter going through the particulate material disturbs it, the probability is increased that the variable constituents will not be present in the sample in exactly the same proportions that they are on the belt. Such a sample collector will tend to selectively reject by particle size or shape various pieces of particulate material so that the variable constituents will be obtained in different proportions than they exist in the total mass being sampled.

SUMMARY OF THE INVENTION

The present invention involves a device for periodically obtaining samples of particulate material from a moving belt wherein the effective opening of the sample cutter is maximized by the relationship of the moving sampler cutter and the moving belt containing the particulate material. This is accomplished in a variety of ways discussed in more detail hereinafter.

It is therefore an object of this invention to maximize the effective opening of a sampler cutter as it transverses a moving belt of particulate material.

It is a further object of this invention to minimize the accumulation of particulate material in front of said sample cutter as it moves across said moving belt.

It is still another object of this invention to minimize the accumulation of particulate material on the upstream side of the sample cutter as compared with the movement of the particulate material on the belt.

These, together with other objects and advantages of the invention will become more readily apparent to those skilled in the art when the following general statements and descriptions are read in the light of the appended drawings.

BRIEF DESCRIPTION OF THE DRAWINGS

FIG. 1 is a perspective view showing a conventional belt sampler, sometimes referred to as a bucket sampler, which is commonly used to sample particulate material.

FIG. 2 is a side elevation view in section showing a sweep-or hammer-type sampler.

FIG. 3 is a plan view of the sampler showing FIG. 2.

FIG. 4 is a sectional plan view of the sampler shown in FIGS. 2 and 3 after the sampler has partially traversed the moving belt.

FIG. 5 is a schematic view of one species of the sampler of applicant's invention.

FIG. 6 is a schematic view of another species of applicant's invention.

FIG. 7 is a schematic view of still another species of applicant's invention.

FIG. 8 is a schematic view of still another species of applicant's invention.

DETAILED DESCRIPTION OF THE INVENTION

Referring now to the drawings and more particularly to FIG. 1, a typical drop sampler is shown with a moving belt 10 which rotates about an appropriate spindle 11 and the particulate material 12 falls or drops off the end of the moving belt 10 and a sample of the particulate material 12 is obtained in the sampling bucket 13 by passing it under the falling particlate material 12 in the direction of the arrow. The particulate material 12 not picked up by the sampling bucket 13 falls to another moving belt where it is carried on through the processing operation.

Referring now to FIG. 2, the particulate material 12 is shown traveling on a typical belt 14 supported by rollers 15—15. The swing- or hammer-type sampler cutter 16 rotates about shaft 17 in housing 18 which is part of sampling unit 18a and as the sampler cutter 16 swings across the surface of the belt 14 in the direction of the arrow it scoops up a sample which is discharged through chute 19.

A plan view of this device in section in FIG. 3 shows the sample cutter 16 in a position where it has just completed a swing across the belt 14 and has deposited particulate material 12 into chute 19. It will be noted that because of the speed of the belt 14 moving in the direction of the arrow and the fact that the sample cutter 16 moves at right angles to the belt 14, the resultant track of the sample being selected is shown at 20 in the form of a diagonal.

FIG. 4 shows a detail of the effect of the relative movement of the sample cutter 16 and the belt 14 in the direction of arrows shown as it affects the particulate material 12. It will be noted that the particulate material 12 in front of the sample cutter 16 as shown at 21 is bunched up as a result of the snowplow effect of the movement of the sample cutter 16 across the belt 14. Likewise, because the belt 14 is moving at right angles to the sample cutter 16, the particulate material 16 in the area of 22 will tend to be packed together and the net result of this is that the coal is distributed and the probability that the variable constituents will not be in the sample in the same proportions as the mass being sampled is greatly increased.

The effective opening of a sample cutter is established by the vector relationships of the speed of the belt holding the stream of particulate material that the cutter is moving through and the speed of the cutter itself. The greater the difference in the two speeds the narrower effective opening so that, for example, if the cutter were stationary and the belt were moving the cutter would have a zero percent effective opening. On the other hand, if the belt were stationary and the cutter were moving, the sample cutter would have a 100 percent effective opening.

Referring now to FIG. 5, it will be seen that the sample cutter 23 of the present invention shown in section is provided with an upstream side 24 whose length may be varied by means of sliding member 25 on tightening pin 26. Alternatively, the length of upstream side 24 of the sample cutter 23 may be maintained fixed in length and the downstream side 24a of sample cutter 23 may be lengthened to accomplish the same result, or the upstream side 24 might be shortened as the downstream side 24a of sample cutter 23 is lengthened. For a given set of parameters, of course, the upstream side 24 of the sample cutter 23 may be fixed in length and shorter than the length of the downstream side 24a of the sample cutter 23, rather than rely on the adjustable features set forth above. The belt 14 is moving in the direction of the arrow shown and the sample cutter 23 is moving at right angles thereto as shown by the arrow associated with the sample cutter 23. The net effect will be to obtain a diagonal track 27 in cutting through the particulate material 12 on the belt 14. However, because the downstream side 24 of the sample cutter 23 can be changed in length, depending on its speed of movement and the speed of movement of the belt 14, the effective opening of the sample cutter 23 is increased considerably as compared with the effective opening of sample cutter 16 of the conventional sweep- or hammer-type.

In FIGS. 5-8, the effective position of the sampling unit 18a is shown in dotted outline.

Referring now to FIG. 6, the sample cutter 23 is tilted toward the direction of movement of the belt 14 as shown by the arrows and the angle of attack of the sample cutter 23 may be varied as shown by arrow 28 depending upon the speed of the belt 14 and the transverse speed of the sample cutter 23 moving across the belt in the direction of the associated arrow. By adjusting these three variables the effective opening of the sample cutter 23 may be optimized even though the diagonal track 27 is made.

Referring now to FIG. 7, the sample cutter 23 is so positioned that it transverses the belt 14 at an angle to the movement of the belt 14 as shown by the respective arrows but may have its speed and angle of attack so adjusted that the net result is that the transverse cut 27 made in the particulate materials 12—12 is essentially the same as if the belt 14 had been stationary, thus maximizing the effective opening of the sample cutter 23.

Referring now to FIG. 8, the sample cutter 23, and associated mechanism 18a, is mounted on two tracks 29—29 that are parallel to belt 14. Thus the sample cutter 23 is accelerated in the same direction as the movement of the belt 14 until it reaches a speed equal to the belt 14 spaced at which time it traverses the belt 14 taking a sample of particulate material 12 in the transverse cut 27 and then the cycle is repeated with suitable mechanism well within the skill of a person skilled in this art, which mechanism is not shown. This does not require much space to function.

EXAMPLE

A typical belt speed is 120 inches per second. A typical sample cutter cross speed is 100 inches per second. A typical belt width is 60 inches, thus the sample cutter's residence time on the belt is 6/10th of a second at a belt speed of 120 inches per second. This would mean that the sample cutter would have to travel 72 inches in the same direction as the belt. This is, of course, six feet. It is well within the skill of the art to accelerate a light mass like this from zero to 120 inches per second in six feet, and decelerate to zero speed also in six feet so that the total distance for this mechanism on the belt would have to be 18 feet, which is quite feasible in all installations.

Thus it will be seen that applicant has shown a variety of ways in which the effective opening of the sample cutter traversing a moving belt of particulate material may be optimized resulting in increasing the probability that the variable constituents on the belt will be present in the sample in exactly the same proportions as the mass being sampled.

While this invention has been described in it preferred embodiment, it is to be appreciated that variations therefrom may be made without departing from the true scope and spirit of the invention.

What is claimed is:

1. A device for periodically obtaining samples of particulate material from a moving belt comprising a sample cutter provided with an opening at one end, means for moving said sample cutter across said moving belt, said sample cutter being provided with at least one adjustable side, which side may be modified so that the length of the downstream side of said sample cutter is greater than the length of the upstream side of said sample cutter, depending upon the speed of the belt and the speed of the sample cutter moving across the belt for maximizing the effective opening of said sample cutter.

2. A device for periodically obtaining samples of particulate material from a moving belt comprising a sample cutter provided with an opening at one end, means for moving said sample cutter across with moving belt, said sample cutter being positioned at an acute angle to the direction of movement of said belt, and means for moving said sample cutter across said moving belt at essentially a right angle thereto.

3. A device for periodically obtaining samples of particulate material from a moving belt comprising a sample cutter provided with an opening at one end, means for moving said sample cutter across said moving belt, said sample cutter being provided with an upstream side shorter in length than the downstream side of said sample cutter, the relative lengths of said sides depending upon the speed of the belt and the speed of the sample cutter moving across the belt for maximizing the effective opening of said sample cutter.

* * * * *

UNITED STATES PATENT AND TRADEMARK OFFICE
CERTIFICATE OF CORRECTION

PATENT NO. : 4,790,196

DATED : December 13, 1988

INVENTOR(S) : Gregory Gould

It is certified that error appears in the above-identified patent and that said Letters Patent is hereby corrected as shown below:

Column 4, line 6, replace the word "spaced" with the word "speed".

Column 4, line 53, replace the word "with" with the word "said".

Signed and Sealed this

Thirtieth Day of May, 1989

Attest:

DONALD J. QUIGG

Attesting Officer

Commissioner of Patents and Trademarks